Figure 1:
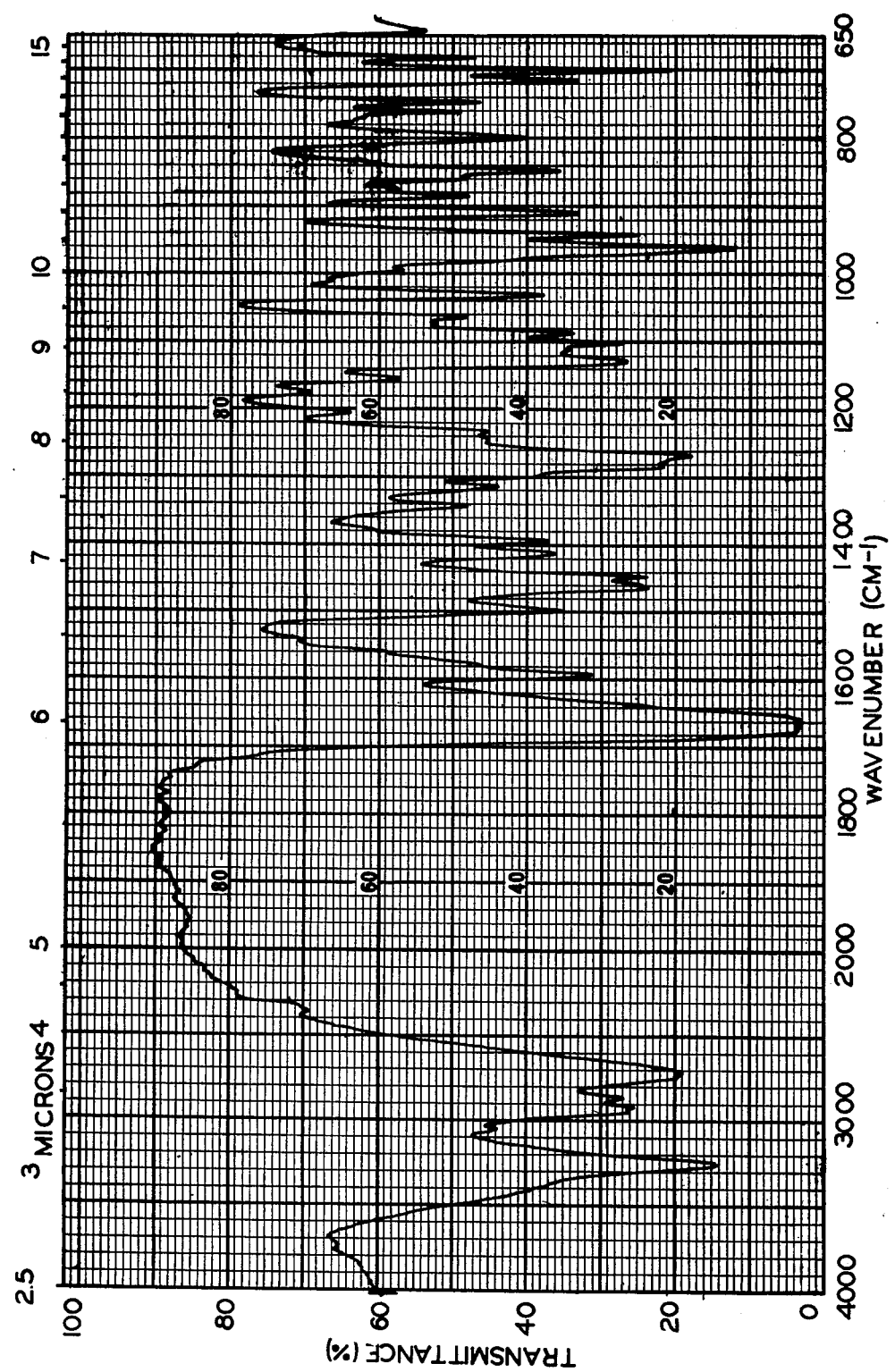
Figure 2:
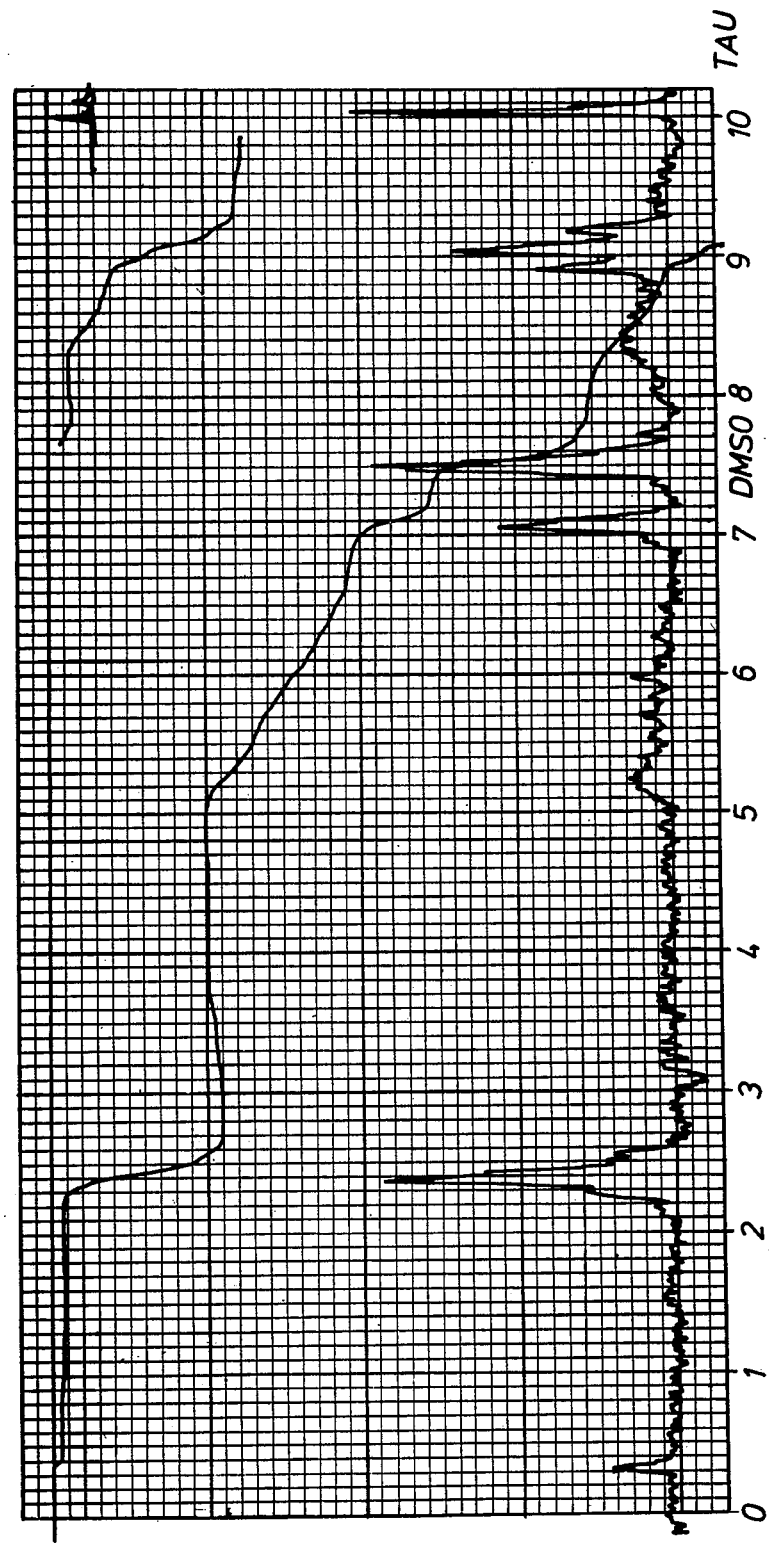
Figure 3:
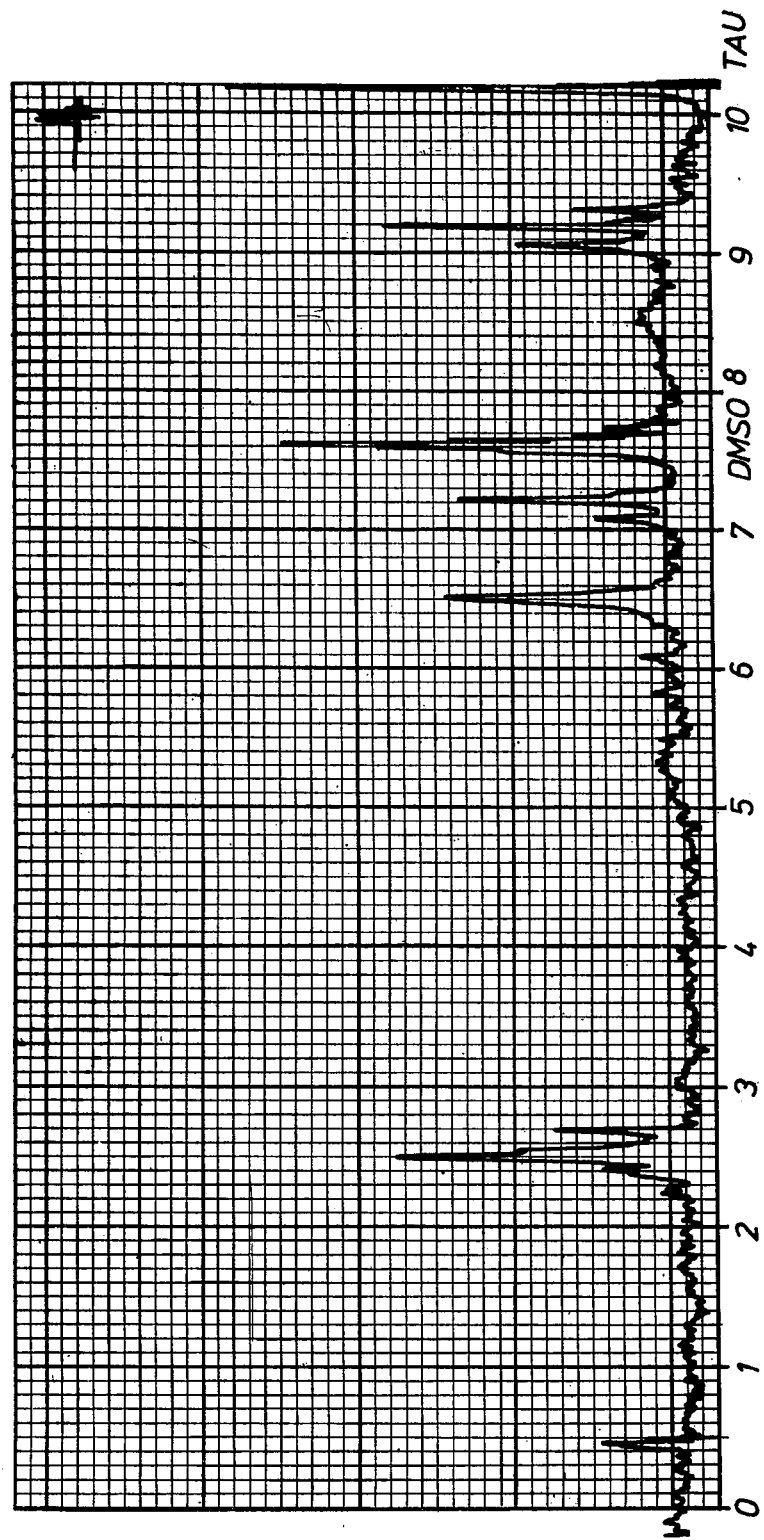
Figure 4:
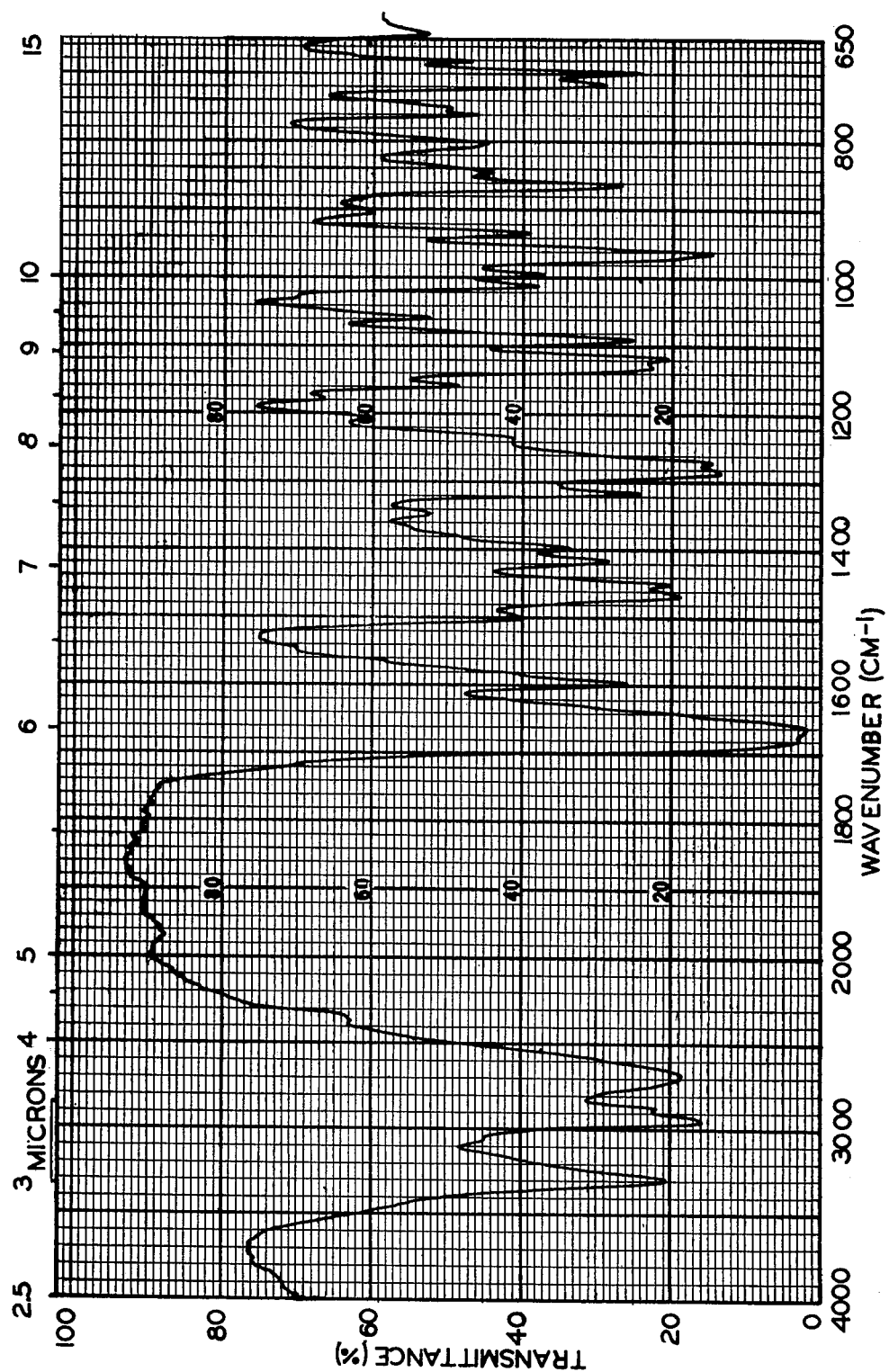
Figure 5:
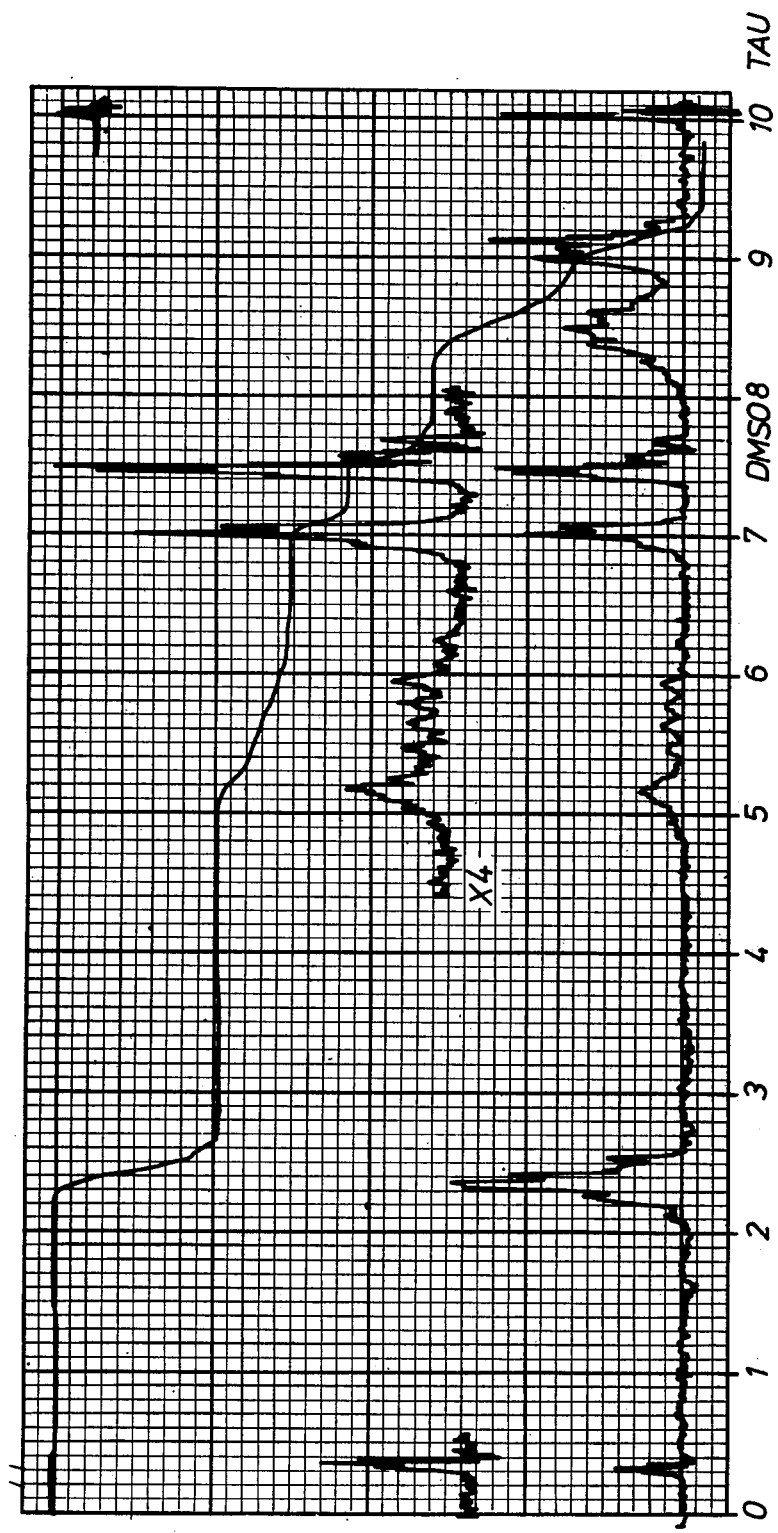

BENZODIAZEPINES

This is a division, of application Ser. No. 576,921, filed May 12, 1975, now U.S. Pat. No. 4,061,745.

BACKGROUND OF THE INVENTION

The novel 1,4-benzodiazepine-4-oxide aldehyde adducts of the invention are aldehyde adducts of benzodiazepines unsaturated at the 1 position, referred to as 3H-1,4-benzodiazepines. 3H-1,4-benzodiazepines are known, and are useful as sedatives and tranquilizers in the field of human therapy. The azeto- [1,4]- benzodiazepine ring structure is an entirely new heterocyclic ring structure.

SUMMARY OF THE INVENTION

It is an object of the invention to provide novel aldehyde adducts of 1,4-benzodiazepin-4-oxides which are useful in the fields of human and animal therapy and as intermediates in the preparation of other useful compounds.

It is also an object of the invention to provide novel azeto-[1,4]-benzodiazepine compounds which are themselves useful in both of the above fields of therapy.

The novel aldehyde adducts of 1,4-benzodiazepine-4-oxides of the invention have the general formula I.

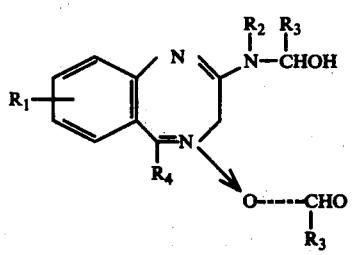

in which the symbols are as defined below. The parent 1,4-benzodiazopino-4-oxides have the general formula II

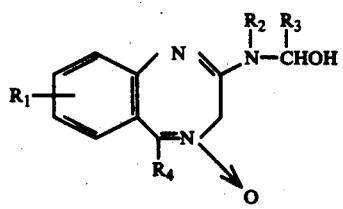

in which the symbols are as defined below. The novel azeto-[1,4]-benzodiazepines of the invention have the general formula III

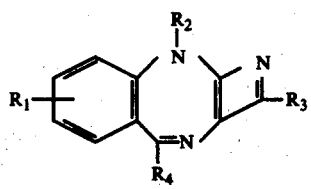

in which the symbols are as defined below.

In the above formula I to III:

$R_1$ represents a hydrogen or halogen atom or a trifluoromethyl, cyano, nitro, lower alkyl, lower alkoxy or lower alkylthio group;

$R_2$ represents a lower alkyl, hydroxy-(lower alkyl), lower alkenyl or benzyl group;

$R_3$ represents a lower alkyl group; and $R_4$ represents a phenyl, (lower alkyl)-phenyl, nitrophenyl, halophenyl or pyridyl group.

As used herein, the term "halogen" means bromine, chlorine, fluorine, or iodine. The term "lower alkyl" refers to both straight-chain and branched-chain alkyl groups containing from 1 to 10 carbon atoms, for example, methyl, ethyl, n-propyl, iso-propyl, n-butyl, n-amyl and n-hexyl. The term "lower alkenyl" means both straight-chain and branched-chain alkenyl groups containing from 2 to 6 carbon atoms, for example vinyl, allyl, butenyl, hexenyl and isobutenyl.

The compounds of the general formula I and their acid addition salts are products in which there can be identified by infrared and proton magnetic resonance spectroscopy the elements of a benzodiazepine ring and the proton magnetic resonance spectrum of which shows a shift at about $\delta = 9.7$ p.p.m. assignable to the aldehydic protons.

The compounds I can be prepared according to the invention by reacting, in aqueous acid, a solution of a 1,4-benzodiazepine-4-oxide of the general formula IV

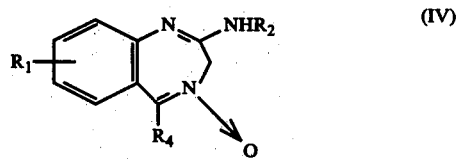

(in which the symbols are as above defined) with an excess, preferably 3 or more molar equivalents, of an aldehyde having the general formula $R_3 CHO$ in which $R_3$ is as above defined. The compound IV is preferably used in solution in aqueous hydrochloric acid, in which case the product is the hydrochloride salt, V

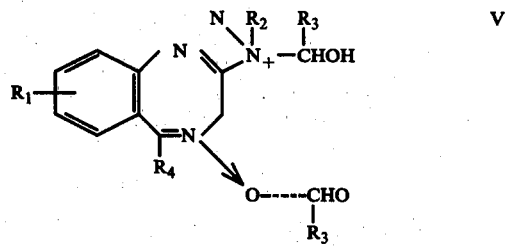

The compound IV or its hydrochloride salt is preferably dissolved in aqueous hydrochloric acid so as to provide a molar ratio of acid: base of 2 or more. The amount of water should be sufficient to ensure that the compound remains in solution, from 300 to 500 ml of water generally being sufficient to dissolve 1 mole of compound IV.

The aldehyde $R_3$—CHO is preferably added in an amount of 3 to 6 moles, advantageously about 4 moles, per mole of compound IV. Stirring is preferably continued for up to 72 hours, generally 60 to 72 hours, at room temperature to enable the reaction to proceed sufficiently near to completion. The product generally precipitates gradually during this time. If no precipitate forms even after 72 hours, the reaction mixture may be stirred with methylene dichloride for 24 hours, during which a crystalline product is generally precipitated. If no precipitate forms even after this treatment, the meth-

| δ(p.p.m.) | | Assignation to: |
|---|---|---|
| 0.76–1 (complex multiplet) | —CH$_3$ | } Two-CH$_2$CH$_2$CH$_3$ groups |
| 1.3–1.74 (complex multiplet) | —CH$_2$— | |
| 2.97 (doublet) | —N—CH$_3$ | |
| 3.75–4.95 (complex multiplet) | | |
| 7.46–7.8 (complex multiplet) | aromatic protons. | |
| 9.68 (broad singlet) | aldehydic proton. | |

Figure 6:
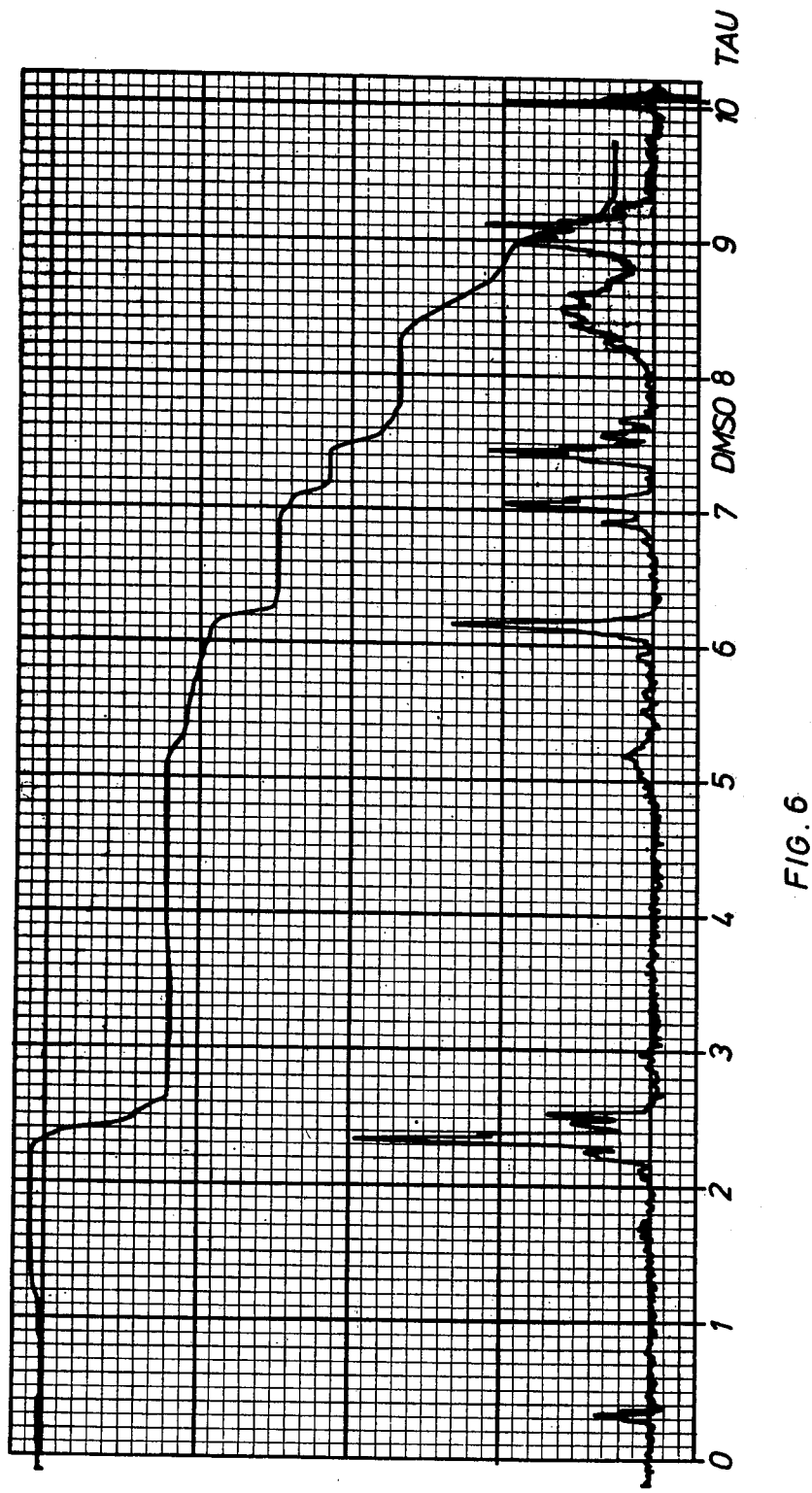

The NMR spectrum after deuteration is shown in FIG. 6 of the drawings and shows that although there are exchangeable protons, as indicated by the additional shift at (δ=3.85 p.p.m.) for example, there is no change on deuteration in the shift at (δ=9.68 p.p.m.). Exchangeable protons may be the protons of the hydrogen chloride salt and of the hydroxy group.

EXAMPLE 3

The product of Example 1, the n-propionaldehyde adduct of 7-chloro-2-(N-methyl-1-hydroxypropylamino)-5-phenyl-3H-1,4-benzodiazepine-4-oxide hydrochloride, (1 g) was dissolved by refluxing for 5 to 10 minutes with isopropyl alcohol (15 ml) and left at room temperature for two days to evaporate. The crystals which formed were collected and triturated with a mixture of methanol and ether. The yield of 7-chloro-2-(N-methyl-1-hydroxypropylamino)-5phenyl-3H-1,4-benzodiazepine-4-oxide hydrochloride (compound II; R$_1$=chlorine in the 7-position; R$_2$=methyl; R$_3$=ethyl; R$_4$=phenyl) was 240 mg. M.P. 192°–4° (with decomposition). The I.R. spectrum was identical to a sample prepared as described in Example 2 of British Patent No. 1,359,287.

EXAMPLE 4

The product of Example 2, the n-butyraldehyde adduct of 7-chloro-2-(N-methyl-1-hydroxybutylamino)-5-phenyl-3H-1,4-benzodiazepine-4-oxide hydrochloride, (500 mg) was dissolved by refluxing for 5 to 10 minutes with isopropyl alcohol (5 ml) and left at room temperature for two days to evaporate. The gummy residue was triturated with a mixture of methanol and ether. The yield of crystalline product of 7-chloro-2-(N-methyl-1-hydroxybutylamino)-5-phenyl-3H-1,4-benzodiazepine-4-oxide hydrochloride (compound II; R$_1$=chlorine in the 7-position; R$_2$=methyl; R$_3$=n-propyl; R$_4$=phenyl) was 50 mg, melting at 194° C. to 195° C. with decomposition. The I.R. spectrum was identical to a sample prepared as described in Example 3 of British Pat. No. 1,359,287.

EXAMPLE 5

40% aqueous sodium hydroxide solution (6 ml) was added to a stirred suspension or solution of the n-propionaldehyde adduct of 7-chloro-2-(N-methyl-1-hydroxypropylamino)-5-phenyl-3H-1,4-benzodiazepine-4-oxide hydrochloride of Example 3 (4.5 g) in methanol (120 ml). The mixture was left standing for 18 hours at room temperature. Crystals that precipitated were filtered and washed with a little methanol followed by water. The yield of pale yellowish crystals of 6-chloro-2-ethyl-9-methyl-4-phenyl-9H-azeto-[2,3-b][1,4]-benzodiazepine (compound III; R$_1$=chlorine in the 6-positon; R$_2$=methyl; R$_3$=ethyl; R$_4$=phenyl) was 2 g, M.P. 194° C. to 195° C. This material contains a trace of methanol as solvent of crystallisation.

The results of analysis were as follows: Calculated for C$_{10}$H$_{16}$Cl N$_3$: C=70.9%; H=5.0%; N=13.1%
Found: C=70.7%; H=5.2%; N=13.0%

EXAMPLE 6

40% aqueous sodium hydroxide solution (6 ml) was added to a stirred solution of the n-butyraldehyde adduct of 7-chloro-2-(N-methyl-1-hydroxybutylamino)-5-phenyl-3H-1,4-benzodiazepine-4-oxide hydrochloride of Example 4 (4.8 g) in methanol (60 ml). The mixture was left standing for 18 hours at room temperature. Crystals that precipitated were filtered and washed with a little methanol followed by water. The yield of needle-like soft crystals of 6-chloro-9-methyl-4-phenyl-2-propyl-9H-azeto[2,3-b][1,4]-benzodiazepine (compound III; R$_1$=chlorine in the 6-position; R$_2$=methyl; R$_3$=n-propyl; R$_4$=phenyl) was 1.5 g, M.P. 179° C. to 180° C.

The results of analysis were as follows:
Calculated for C$_{20}$H$_{18}$ClN$_3$: C=71.5%; H=5.4%; N=12.5% Found: C=71.2% H=5.4%; N=12.6%

EXAMPLE 7

The 6-chloro-2-ethyl-9-methyl-4-phenyl-9H-azeto-[2.3-b][1,4] benzodiazepine of Example 5 (322 mg) was treated with a saturated methanolic hydrogen chloride solution (10 ml) and diluted with diethyl ether to obtain colourless crystals. The yield of the hydrochloride salt of 6-chloro-2-ethyl-4-phenyl-9-methyl-9H-azeto-[2,3-b][1,4]-benzodiazepine was 300 mg. The product melted at 189° C. to 190° C. with decomposition.

EXAMPLE 8

The 6-chloro-9-methyl-4-phenyl-2-propyl-9H-azeto-[2,3-b][1,4]-benzodiazepine of Example 6 (336 mg) was treated with saturated methanolic hydrogen chloride (10 ml) and diluted with diethyl ether to obtain colourless crystals. The yield of the hydrochloride salt of 6-chloro-9-methyl-4-phenyl-2-propyl-9H-azeto-[2,3-b][1,4]-benzodiazepine was 270 mg. The product melted at 183° C. to 184° C. with decon position.

What we claim is:
1. A compound of the formula

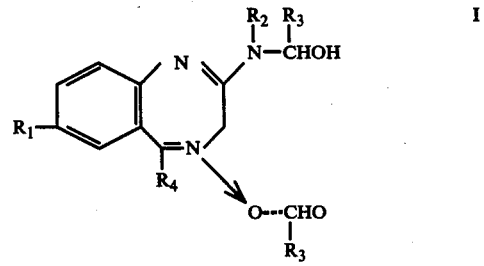

wherein $R_1$ represents hydrogen, halogen, a trifluoromethyl group, cyano, nitro, lower alkyl, lower alkoxy or lower alkylthio group;

$R_2$ represents lower alkyl, hydroxy-(lower alkyl), lower alkenyl or a benzyl group;

$R_3$ represents a lower alkyl group; and $R_4$ represents phenyl, (lower alkyl)-phenyl, nitrophenyl, halophenyl or a pyridyl group.

2. The n-propionaldehyde adduct of 7-chloro-2-(N-methyl-1-hydroxypropylamino)-5-phenyl-3H-1,4-benzodiazepine-4-oxide hydrochloride.

3. The n-butyraldehyde adduct of 7-chloro-2-(N-methyl-1-hydroxybutylamino)-5-phenyl-3H-1,4-benzodiazepine-4-oxide hydrochloride.

4. A compound according to claim 1 wherein $R_4$ is phenyl.

5. A compound according to claim 4 wherein $R_1$ is chlorine.

6. A compound according to claim 5 wherein $R_2$ is methyl or ethyl.

7. Process for the preparation of a compound according to claim 1 which comprises reacting an aqueous solution of a 1,4-benzodiazepine-4-oxide of the formula

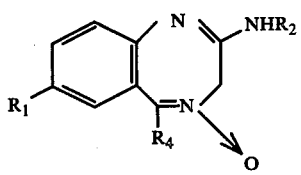

wherein $R_1$ represents hydrogen, haloen, a trifluoromethyl group, cyano, nitro, lower alkyl, lower alkoxy or lower alkylthio group;

$R_2$ represents a lower alkyl radical; and $R_4$ represents a phenyl, (lower alkyl)-phenyl, nitrophenyl, halophenyl or pyridyl group with an aldehyde having the general formula $R_3CHO$ in which $R_3$ represents a lower alkyl group, the mol ratio of said aldehyde to said 1,4-benzodiazepine-4-oxide being at least 3:1.

8. A process according to claim 7, carried out at or below room temperature.

9. A process according to claim 7 wherein $R_4$ is phenyl.

10. A process according to claim 9 wherein $R_1$ is chlorine.

11. A process according to claim 10 wherein $R_2$ is methyl or ethyl.

12. A process for producing a compound of the formula

V $R_1$ is hydrogen, halogen, a trifluoromethyl group, cyano, nitro, lower alkyl, lower alkoxy or a lower alkylthio group;

$R_2$ is a lower alkyl, hydroxy-(lower alkyl), lower alkenyl or benzyl group;

$R_3$ represents a lower alkyl group; and $R_4$ represents phenyl, (lower alkyl)-phenyl, nitrophenyl, halophenyl or a pyridyl group which comprises contacting 1,4-benzodiazepine-4-oxide of the formula

IV wherein $R_1$, $R_2$ and $R_4$ have the previously assigned significance with at least 3 mols of an aldehyde of the formula $R_3CHO$ wherein $R_3$ is a lower alkyl group per mol of said 1,4-benzodiazepine compound, in the presence of an aqueous hydrochloric acid.

13. A therapeutic composition comprising a tranquilizing, sedating or hypnotizing amount of a compound of the formula

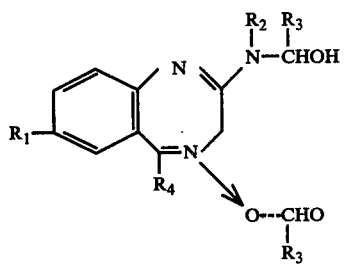

wherein $R_1$ represents hydrogen, halogen, a trifluoromethyl group, cyano, nitro, lower alkyl, lower alkoxy or lower alkyl thio group;

$R_2$ represents lower alkyl, hydroxy-(lower alkyl), lower alkenyl or a benzyl group;

$R_3$ represents a lower alkyl group; and $R_4$ represents phenyl, (lower alkyl)-phenyl, nitrophenyl, halophenyl, a pyridyl group, or an acid addition salt thereof in admixture with a pharmacologically acceptable diluent or carrier.

* * * * *

UNITED STATES PATENT AND TRADEMARK OFFICE
CERTIFICATE OF CORRECTION

PATENT NO. : 4,145,417
DATED : March 20, 1979
INVENTOR(S) : SHENOY

It is certified that error appears in the above—identified patent and that said Letters Patent are hereby corrected as shown below:

Column 2, line 42, Compound V, under "$\underset{\underset{CHOH}{|}}{R_3}$" insert -- $Cl^-$ --.

Column 5, line 29, after "5" insert -- - --.

Column 6, line 53, "decon position" should read -- decomposition --.

Column 7, line 40, "haloen" should read -- halogen --.

*Signed and Sealed this*

*Twenty-eighth* Day of *August 1979*

[SEAL]

Attest:

LUTRELLE F. PARKER
*Attesting Officer*  *Acting Commissioner of Patents and Trademarks*

UNITED STATES PATENT AND TRADEMARK OFFICE
CERTIFICATE OF CORRECTION

PATENT NO. : 4,145,417
DATED : March 20, 1979
INVENTOR(S) : SHENOY

It is certified that error appears in the above-identified patent and that said Letters Patent are hereby corrected as shown below:

Column 2, line 42, Compound V, under "$R_3$" insert -- $Cl^-$ --.
$\phantom{Column 2, line 42, Compound V, under "R_3}|3$
$\phantom{Column 2, line 42, Compound V, under "R_3}CHOH$ Column 5, line 29, after "5" insert -- - --.

Column 6, line 53, "decon position" should read -- decomposition --.

Column 7, line 40, "haloen" should read -- halogen --.

*Signed and Sealed this*

*Twenty-eighth* Day of *August 1979*

[SEAL]

Attest:

LUTRELLE F. PARKER
*Attesting Officer*    *Acting Commissioner of Patents and Trademarks*